United States Patent [19]
Adjei et al.

[11] Patent Number: 5,676,931
[45] Date of Patent: Oct. 14, 1997

[54] AEROSOL DRUG FORMULATIONS FOR USE WITH NON CFC PROPELLANTS

[75] Inventors: Akwete L. Adjei, Wadsworth; Pramod K. Gupta, Gurnee; Mou-Ying Fu Lu, Lake Bluff, all of Ill.

[73] Assignee: Abbott Laboratories, Abbott Park, Ill.

[21] Appl. No.: 655,275

[22] Filed: May 15, 1996

Related U.S. Application Data

[63] Continuation of Ser. No. 161,115, Dec. 2, 1993, abandoned.

[51] Int. Cl.$^6$ ........................................ A61K 9/12
[52] U.S. Cl. ........................ 424/45; 424/46; 514/937
[58] Field of Search ........................ 424/43, 45, 46; 514/958, 937

[56] References Cited

U.S. PATENT DOCUMENTS

| | | |
|---|---|---|
| 5,202,110 | 4/1993 | Dalby et al. ........................ 424/45 |
| 5,225,183 | 7/1993 | Purewal et al. ........................ 424/45 |
| 5,230,884 | 7/1993 | Evans et al. ........................ 424/45 |

FOREIGN PATENT DOCUMENTS

| | | |
|---|---|---|
| WO91/11173 | 4/1991 | WIPO . |
| WO92/00061 | 1/1992 | WIPO . |
| WO92/00107 | 1/1992 | WIPO . |
| WO92/08447 | 5/1992 | WIPO . |
| WO92/14444 | 9/1992 | WIPO . |

OTHER PUBLICATIONS

Movén, F. et al. (1993). Aerosols in Medicine. Elsevier Science Publishers B.V, pp. 303–319.

*Primary Examiner*—Raj Bawa
*Attorney, Agent, or Firm*—Mona Anand

[57] ABSTRACT

Pharmaceutical compositions for aerosol delivery comprising a medicament, a non-chlorofluorocarbon propellant and a protective colloid, as well as a method for preparing such compositions in which the aggregation of the particles is prevented without the use of surfactants or cosolvents.

22 Claims, No Drawings

AEROSOL DRUG FORMULATIONS FOR USE WITH NON CFC PROPELLANTS

CROSS REFERENCE TO RELATED APPLICATIONS

This is a continuation of U.S. Ser. No. 08/161,115 filed Dec. 2, 1993, now abandoned.

The present invention relates to drug formulations for aerosol delivery which are compatible with non-chlorofluorocarbon propellants, and especially to excipients which are useful therein. In particular, the invention relates to formulations comprising protective colloids which possess improved physical stability and provide uniform dosing without the use of cosolvents and/or emulsifying carrier additives.

BACKGROUND OF THE INVENTION

Numerous pharmaceutical compounds are preferentially delivered by means of metered dose inhalation (MDI) devices, in which a physiologically inert propellant of high vapor pressure is used to discharge a precise amount of medication with each operation. These MDI devices, also known as aerosols or inhalers, have found widespread use among patients suffering, for example, from episodic or chronic asthma. The propellants of choice have historically been chlorofluoro-carbons, such Propellant 11 (trichlorofluoromethane), Propellant 12 (dichlorodifluoromethane) and Propellant 114 (dichlorotetrafluoroethane).

In recent years, however, there have been growing concerns that chlorofluorocarbon (CFC) propellants have detrimental environmental effects, and in particular that they interfere with the protective upper-atmosphere ozone layer. Under an international accord (the Montreal Protocol), the use of CFC propellants will be prohibited by the start of the year 2000, and possibly sooner. Alternative propellant vehicles are being developed which exhibit little or no ozone depletion potential (ODP). Such alternative propellants include two—HFC-134a (1,1,1,2-tetrafluoroethane) and HFC-227ea (1,1,1,2,3,3,3-heptafluoropropane)—which have ODPS of zero and are currently undergoing safety and environmental testing.

Unfortunately, surfactants which are generally used in known MDI formulations have been found to be imiscible in and therefore incompatible with these new, non-CFC propellants. Such surfactants are necessary to prevent aggregation (in the form of "caking" or crystallization, for example) of the medicinally active compound in the reservoir of the inhaler, and to facilitate uniform dosing upon aerosol administration. To overcome this incompatibility, it has previously been taught to include cosolvents (such as ethanol) with the non-CFC propellants so as to blend the surfactants into the formulation. Another suggested approach has been to emulsify the MDI formulation in the presence of a surfactant with low-vapor pressure additives, such as polyhydroxy alcohols as for example propylene glycol.

Such cosolvents or additives may of course be physiologically active, and in some instances may not be tolerated by the user of an MDI medication. There is therefore a need for MDI formulations compatible with non-CFC, non-ozone depleting propellants, which prevent aggregation of drug particles without the use of cosolvents or similar carrier additives.

SUMMARY OF THE INVENTION

It has now been found that certain non-conventional pharmaceutical excipients, herein referred to as protective colloids, are capable of stabilizing MDI formulations utilizing the propellants HFC-134a and HFC-227ea so as to prevent aggregation and provide dosing uniformity without the need for either surfactants or cosolvents. These protective colloids are amphiphilic agents which—unlike most surfactants—do not dissolve, but instead are finely dispersed solids. While not intending to be limited by theory, it is believed that their action is due to molecular size and surface properties, such as charge and lipophilicity.

The protective colloids described herein are biocompatible and present no known toxicologic or pathologic consequences at the concentrations proposed for their use. Non-CFC formulations which include protective colloids do not require the addition of cosolvents or even of conventional surfactants such as sorbitan trioleate (SPAN 85), sorbitan monooleate and oleic acid, yet provide high lung deposition efficiencies and respirable fractions comparable to those obtained with known CFC-propellant formulations. It is thus expected that non-CFC formulations comprising protective colloids will be useful for the delivery of both peptide and non-peptide pharmaceutical medicaments for which MDI delivery is deemed favorable.

Accordingly, in one aspect of the present invention are disclosed pharmaceutical compositions for aerosol delivery, as for example by inhalation and pulmonary absorption, comprising a therapeutically effective amount of a medicament, a non-chlorofluorocarbon propellant, and a protective colloid. The propellant in such compositions are preferably fluorocarbons and, more preferably, the non-ozone depleting fluorocarbons HFC-134a or HFC-227ea. The medicament in the compositions of the invention are preferably LHRH analogs or 5-lipoxygenase inhibitors; especially preferred medicaments include leuprolide acetate and the 5-lipoxygenase inhibitors R(+)-N-[3-[5-(4-fluorophenoxy)-2-furanyl]-1-methyl-2-propynyl]-N-hydroxyurea and R(+)-N-[3-[5-(4-fluorophenoxy)-thiophen-2-yl]-1-methyl-2-propynyl]-N-hydroxyurea. (As used herein, "5-lipoxygenase inhibitor" refers to any physiologically active compound capable of affecting leukotriene biosynthesis.)

In the pharmaceutical compositions of the invention, the protective colloid may be selected from among substituted, mixed, and esterified organic alcohols; substituted and mixed organic acids; substituted alkylsulfates; substituted alkylsulfonates; alkylsulfosuccinates; cholic acid derivatives; glyceride esters of fatty acids; glyceride esters of polyethylene glycol acids; polyoxyethylene ethers, alcohols and esters; alkyl-substituted sorbitol esters and ethers with organic acids; stearates; and substituted organic stearates.

Alternatively, and in particular when the medicament is an LHRH analog such as leuprolide acetate, the protective colloid may be chosen from hydrolyzed poly(vinyl alcohol)s, phosphatic acid, cholesterol, tripalmitin (glyceryl tripalmitate) and biological detergents, where preferred biological detergents include anionic detergents, zwitterionic detergents and polyoxyethylene ether nonionic detergents. Of these, hydrolyzed poly(vinyl alcohol), sodium lauryl sulfate, phosphatic acid, cholesterol, tripalmitin and decanesulfonic acid are preferred protective colloids, and sodium lauryl sulfate, cholesterol, tripalmitin and decanesulfonic acid are especially preferred.

As a further alternative, and particularly when the medicament is a 5-lipoxygenase inhibitor such as R(+)-N-[3-[5-(4-fluorophenoxy)-2-furanyl]-1-methyl-2-propynyl]-N-hydroxyurea or R(+)-N-[3-[5-(4-fluorophenoxy)-thiophen-2-yl]-1-methyl-2-propynyl]-N-hydroxyurea, the protective colloid of the present invention may be aerosol 22, alkylsulfonic acids, hydrolyzed poly(vinyl alcohol), sodium lauryl sulfate, phosphatic acid, cholesterol, tripalmitin and decanesulfonic acid, hydrolyzed poly(vinyl alcohol), cholesterol, sodium lauryl sulfate, stearic acid, caprylic acid, cholic acid, glycocholic acid, taurocholic acid, deoxycholic acid, glycodeoxycholic acid, taurodeoxycholic acid, polidocanol, TERGITOL polyglycol ether, polyoxyethylene 4-lauryl ether, polyoxyethylene 10-lauryl ether, 1-pentanesulfonic acid, 1-octanesulfonic acid, 1-nonanesulfonic acid, 1-decanesulfonic acid, N-decyl-N,N-dimethyl-3-ammonio-1-propanesulfonic acid, (3-[(3-cholamidopropyl)-dimethylammonio]-1-propanesulfonic acid, (3-[(3-cholamidopropyl)-dimethylammonio]-2-hydroxy-1-propanesulfonic acid or N-hexadecyl-N,N-dimethyl-3-ammonio-1-propanesulfonic acid.

Of these, cholesterol, sodium lauryl sulfate, stearic acid, caprylic acid, taurocholic acid, taurodeoxycholic acid, 1-octanesulfonic acid, 1-nonanesulfonic acid, N-decyl-N,N-dimethyl-3-ammonio-1-propanesulfonic acid, (3-[(3-cholamidopropyl)-dimethylammonio]-1-propanesulfonic acid and (3-[(3-cholamidopropyl)-dimethylammonio]-2-hydroxy-1-propanesulfonic acid are preferred protective colloids, and cholesterol, sodium lauryl sulfate, stearic acid, caprylic acid and taurocholic acid are especially preferred.

The protective colloids of the present invention may be present in a concentration of between about 0.00001% and about 10% by weight, and preferably in a concentration of between about 0.001% and about 5% by weight.

In a further aspect of the present invention is disclosed a method of preparing a stable suspension of particles of a medicament in a liquid phase non-chlorofluorocarbon aerosol propellant, which method comprises the addition to the suspension of a protective colloid in an amount sufficient to prevent aggregation of the particles. Preferably, the protective colloid may be added in an amount of between about 0.00001% and about 10% by weight; more preferably, the protective colloid may be added in an amount of between about 0.001% and about 5% by weight. The propellants, medicaments and protective colloids suitable for use in the method of the present invention are those described above in connection with the pharmaceutical compositions of this invention.

DETAILED DESCRIPTION OF THE INVENTION

It is expected that numerous non-ozone depleting aerosol propellants may be used with the compositions and methods of the present invention. These include not only HFC-134a and HFC-27ea, described above, but also halogenated alkanes in general, such as HCFC-123 (1,1,1-trifluoro-2,2-dichloroethane), HCFC-124 (1,1,1,2-tetrafhorochloroethane), HCFC-141b, HCFC-225, HFC-125, FC-C51-12 (perfluorodimethylcyclobutane), DYMEL A (dimethyl ether) and DYMEL 152a (1,1-difluoroethane).

It is further expected that the compositions and methods of the invention will be suitable for the administration of a wide variety of peptide and non-peptide drugs. Examples of peptides which may be delivered in this fashion are interferons and other macrophage activation factors, such as lymphokines, muramyl dipeptide (MDP), 7-interferon, and interferons a and b, and related antiviral and tumoricidal agents; opioid peptides and neuropeptides, such as enkaphalins, endorphins and dynorphins, and related analgesics; renin inhibitors including new-generation anti-hypertensive agents; cholecystokinins (CCK analogs) such as CCK, ceruletide and eledoisin, and related cardiovascular- and CNS-targeting agents; leukotrienes and prostaglandins, such as oxytocin, and related antiinflammatory, oxytocic and abortifacient compounds; erythropoietin and analogs thereof, as well as related haematinics; LHRH analogs, such as leuprolide, buserelin and nafarelin, and related down-regulators of pituitary receptors; parathyroid hormone and other growth hormone analogs; enzymes, such as DNase, catalase and alpha-1 antitrypsin; GM-CSF and other immunomodulators; and insulin. Such peptides are frequently not well-absorbed when given orally.

Examples of non-peptides which may readily be delivered using the compositions and methods of the present invention are beta-agonists, such as isoproterenol, albuterol, isoetherine and metoproteronol, and related anti-asthmatics; steroids, such as flunisolide, and similar anti-asthmatics; cholinergic agents, such as cromolyn, and related anti-asthmatics; and 5-lipoxygenase inhibitors, such as zileuton and the hydroxyurea compound described above, and related leukotriene inhibitors. Such non-peptides may lend themselves to oral administration, but when given by inhalation are found to produce rapid reversal of bronchoconstriction in cases of allergic airway disease and asthma. Also, these compounds may be administered more frequently as MDI formulations than when given orally.

It is also expected that numerous protective colloids will be identified which are suitable for use in the compositions and methods of the present invention. These include substituted, mixed, or esterified organic alcohols, such as poly(vinyl alcohol)s and polidocanol; substituted or mixed organic acids, such as stearic, capric and caprylic acids; substituted alkylsuffates, such as cetyl, lauryl, stearyl myristyl and palmityl derivatives, sodium lauryl sulfate, CHAPSO and CHAPS; substituted alkylsulfonates, such as palmityl sulfobetaine SB16; alkylsulfosuccinates, such as dioctylsulfosuccinate; cholic acid derivatives, such as cholic, deoxycholic, glycodeoxycholic, glycocholic, taurocholic and taurodeoxycholic acids; glyceride esters of fatty acids, such as cholesterol; glyceride esters of polyethylene glycol acids, such as LABRAFIL M 2125 CS; polyoxyethylene ethers, alcohols and esters, such as BRIJ 30, 52, 56, 58, 72, 76, 78, 700, 721, 92, 93, 96, 97, 98, 99, etc.; alkyl-substituted sorbitol esters and ethers with organic acids, such as ARLACEL 20, 40, 60, 80, 83, 85, 165, 186 and ARLACEL C and PLURONICS; and stearates and substituted organic stearates, such as stearic acid.

The medicaments useful in the compositions of the present invention include not only those specifically named above, but also where appropriate the pharmaceutically acceptable salts, esters, amides and prodrugs thereof. By "pharmaceutically acceptable salts, esters, amides and prodrugs" is meant those carboxylate salts, amino acid addition salts, esters, amides and prodrugs of a compound which are, within the scope of sound medical judgement, suitable for use in contact with the tissues of humans and lower animals with undue toxicity, irritation, allergic response and the like, commensurate with a reasonable benefit/risk ratio and effective for their intended use.

The term "salts" refers to the relatively non-toxic, inorganic and organic acid addition salts of a medicinal compound. These salts can be prepared in situ during the final isolation and purification of the compound or by separately reacting the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laureate, borate, benzoate, lactate, phosphate, tosylate, citrate, maleate, fumarate, succinate, tartrate, naphthylate, mesylate, glucoheptonate, lactiobionate and laurylsulphonate salts and the like. These may include cations based on the alkali and alkaline earth metals, such as sodium, lithium, potassium, calcium, magnesium and the like, as well as nontoxic ammonium, quaternary ammonium and amine cations including, but not limited to, ammonium, tetramethylammonium, tetraethylammonium, methylamine, dimethylamine, trimethylamine, triethylamine, ethylamine and the like. (See, for example S. M. Berge, et al., "Pharmaceutical Salts," *J. Pharm. Sci.*, 66: 1–19 (1977).)

Examples of pharmaceutically acceptable, non-toxic esters of a compound include ($C_1$-to-$C_6$ alkyl) esters wherein the alkyl group is a straight or branched chain. Acceptable esters also include ($C_5$-to-$C_7$ cycloalkyl) esters as well as arylalkyl esters such as, but not limited to, benzyl; ($C_1$-to-$C_4$ alkyl) esters are preferred.

Examples of pharmaceutically acceptable, non-toxic amides of medicinal compounds include amides derived from ammonia, primary ($C_1$-to-$C_6$ alkyl) amines and secondary ($C_1$-to-$C_6$ dialkyl) amines wherein the alkyl groups are straight or branched chain. In the case of secondary amines the amine may also be in the form of a 5- or 6-membered heterocycle containing one nitrogen atom. Amides derived from ammonia, ($C_1$-to-$C_3$ alkyl) primary amides and ($C_1$-to-$C_2$ dialkyl) secondary amides are preferred. Amides of the compounds of the invention may be prepared according to conventional methods.

The term "prodrug" refers to compounds that are rapidly transformed in vivo to yield the parent medicinal compound, as for example by hydrolysis in blood. A thorough discussion is provided in T. Higuchi and V. Stella, "Pro-drugs as Novel Delivery Systems", Vol 14 of the A.C.S. Symposium Series, and in *Bioreversible Carriers in Drug Design*, ed. Edward B. Roche, American Pharmaceutical Association and Pergamon Press (1987).

When used in the above compositions, a therapeutically effective amount of a medicament of the present invention may be employed in pure form or, where such forms exist, in pharmaceutically acceptable salt, ester or prodrug form. By a "therapeutically effective amount" of a medicament is meant a sufficient amount of the compound to obtain the intended therapeutic benefit, at a reasonable benefit/risk ratio applicable to any medical treatment. It will be understood, however, that the total daily usage of the medicaments and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses at levels lower than required for to achieve the desired therapeutic effect and to gradually increase the dosage until the desired effect is achieved.

The total daily doses of the medicaments contemplated for use with this invention, and consequently the concentrations by weight of the medicaments in the respective compositions, may vary widely. In the case of an LHRH analog, such as leuprolide acetate, the intended daily dose may range from about 0.01 to about 5 mg/day; accordingly, where an aerosol inhaler is to be used several times a day with a discharge volume of between about 5 and about 250 µl, the concentration of medicament will be between about 0.2 and about 20 mg/ml. Similarly, in the case of a 5-lipoxygenase inhibitor expected to be administered in a daily dose ranging from about 0.01 to about 10 mg/kg/day, the concentration will be between about 0.001 and about 100 mg/ml. Of course, medicament concentrations outside of these ranges may also be suitable, where different potencies, dosing frequencies and discharge volumes are used.

The compositions of the invention may be prepared by combining a protective colloid with a medicament which has been milled or otherwise reduced to a desired particle size, and placing the mixture in a suitable aerosol container or vial. After sealing the container, an aerosol propellant is introduced and the system is agitated to fully blend the ingredients. Alternatively, the colloid and medicament may be milled together, either before or after addition of propellant. In some instances, it may be necessary to wet-mill the medicament in a closed system, as for example under temperature and pressure conditions which permit the medicament to be milled while mixed with a liquid-phase aerosol propellant. It is expected that, for any particular combination of medicament, propellant and colloid, the ideal order of addition of ingredients and the conditions under which they are to be combined, may readily be determined.

The compositions and methods of the present invention will be better understood in connection with the following examples, which are intended as an illustration of and not a limitation upon the scope of the invention. Both below and throughout the specification, it is intended that citations to the available literature are expressly incorporated by reference.

EXAMPLE 1

Physical Stability of Compositions Containing Leuprolide Acetate

A determination of the effect of protective colloids on the physical stability of leuprolide acetate in MDI formulations prepared with HFA-134a was conducted as follows: Approximately 0.5% protective colloid was added to drug (~100 mg of leuprolide acetate) in appropriate transparent aerosol containers (vials). The vials were crimped and charged with approximately 10 mL of HFC-134a and homogenized to blend the ingredients. The dispersion quality in each preparation was evaluated visually after 24 and 48 hours. Results are shown below in Table 1; these data show that a number of protective colloids produce good dispersion quality after both 24 and 48 hours. In comparison, control formulations prepared without a protective colloid were seen to have poor dispersion quality after less than 15 seconds.

TABLE 1

Dispersion Quality of Leuprolide Acetate in HFA-134a

| Protective Colloid Used | Dispersion Quality | |
|---|---|---|
|  | 24 Hours | 48 Hours |
| Polyvinyl Alcohol (88%) | Good | Poor |
| Polyvinyl Alcohol (99%) | Good | Poor |

TABLE 1-continued

Dispersion Quality of Leuprolide Acetate in HFA-134a

| Protective Colloid Used | Dispersion Quality | |
|---|---|---|
| | 24 Hours | 48 Hours |
| Decane Sulfonic Acid | Good | Good |
| Sodium Lauryl Sulfate | Good | Good |
| Phosphatidic Acid (Dipalmitoyl) | Good | Poor |
| Cholesterol | Good | Good |
| Tripalmitin | Good | Good |

EXAMPLE 2

Physical Stability of Compositions Containing R(+)-N-[3-[5-(4-fluorophenoxy)-2-furanyl]-1-methyl-2-propynyl]-N-hydroxyurea A determination of the effect of protective colloids on the physical stability of R(+)-N-[3-[5-(4-fluorophenoxy)-2-furanyl]-1-methyl-2-propynyl]-N-hydroxyurea in MDI formulations prepared with HFA-134a was conducted as follows: Approximately 60 mg protective colloid was added to drug (120 mg) in appropriate transparent aerosol containers (vials). The vials were crimped and charged with approximately 10 mL of HFC-134a and homogenized to blend the ingredients. The dispersion quality in each preparation was evaluated visually after 24 and 48 hours. Results are shown below in Table 2; these data show that a number of protective colloids produce good dispersion quality after both 24 and 48 hours. In comparison, control formulations prepared without a protective colloid were seen to have poor dispersion quality after less than 15 seconds.

TABLE 2

Dispersion Quality of HFA-134a and R(+)-N-[3-[5-(4-fluorophenoxy)-2-furanyl-1-methyl-2-propynyl]-N-hydroxyurea in HFA-134a

| Protective Colloid Used | Dispersion Quality | |
|---|---|---|
| | 24 Hours | 48 Hours |
| Brij 30 | Good | Moderately good |
| Stearic Acid | Moderately good | Good |
| Caprylic Acid | Moderately good | Good |
| Taurocholic Acid | Moderately good | Good |
| Cholesterol | Good | Good |
| Taurodeoxycholic Acid | Moderately good | Fairly good |
| 1-Nonanesulfonic Acid | Moderately good | Fairly good |
| Chaps | Moderately good | Fairly good |
| 1-Octanesulfonic Acid | Moderately good | Fairly good |
| N-Decyl-N,N-dimethyl-3-ammonio-1-propanesulfonic Acid | Moderately good | Fairly good |
| Chapso | Good | Fairly good |

EXAMPLE 3

Uniformity of Delivery of Compositions Containing Leuprolide Acetate

Data relating to average shot weight and drug concentration of leuprolide acetate in HFA-134a containing a protective colloid is shown in Table 3. Gravimetric measurements of serially actuated shots of test formulations were made using an analytical balance. Duplicate cans of each formulation were primed by spraying 5 times. The weight of these cans were recorded. Thereafter, 10 sequential shots were made and the cans weighed each time to determine the mean shot weight of each spray. The sprays were collected each time in methanol for use in content uniformity measurements. Shot weights were measured until cans were completely empty of formulation.

Sprays used in the shot weight analysis were collected and analyzed for leuprolide content. The sprays were collected under methanol and directly subjected to HPLC analysis for leuprolide acetate. Multiple sample preparations were chemically analyzed to investigate inter-sample variability. The data shows that formulations containing protective colloids provide consistent shot weights and drug delivery.

TABLE 3

Content Uniformity of Selected Aerosol Formulations of Leuprolide Acetate in HFA-134a

| Protective Colloid Used | Shot weight (mg/spray) | Drug Concentration (µg/mL) |
|---|---|---|
| Polyvinyl Alcohol, PVP (99%) | 58.80 | 661.90 |
| Polyvinyl Alcohol, PVP (88%) | 57.00 | 557.54 |
| Sodium Lauryl Sulfate, SLS | 56.00 | 547.50 |
| Decane Sulfonic Acid, DSA | 56.40 | 580.85 |
| Phosphatidic Acid, PA | 57.00 | 523.16 |
| Cholesterol, CHL | 61.60 | 520.45 |
| Tripalmitin, TP | 61.60 | 552.27 |

EXAMPLE 4

Uniformity of Delivery of Compositions Containing R(+)-N-[3-[5-(4-fluorophenoxy)-2-furanyl]-1-methyl-2-propynyl]-N-hydroxyurea Mean drug content uniformity per spray with formulations containing 12 mg/mL of R(+)-N-[3-[5-(4-fluorophenoxy)-2-furanyl]-1-methyl-2-propynyl]-N-hydroxyurea and 0.6% w/v cholesterol in HFA-134a was determined in duplicate vials. The vials were crimped and then tested for drug content uniformity. Both formulations were primed by spraying 10 times and then weighed. Thereafter, 10 shots were made while immersing the delivery nozzle in a beaker containing 25 mL of ethanol. The ethanol samples were assayed for drug concentration by HPLC after appropriate dilution. The results are shown in Table 4. The results show that for every 10 sprays, approximately 1.2±0.2 mg of drug was uniformly delivered for a total of 130 sprays. The data shows that a cholesterol-based formulation allows uniform delivery of R(+)-N-[3-[5-(4-fluorophenoxy)-2-furanyl]-1-methyl-2-propynyl]-N-hydroxyurea from a HFA-134a based MDI formulation.

TABLE 4

Mean Drug Content Uniformity (mg/spray)

| Number of Sprays | Vial 1 | Vial 2 | Mean ± SEM |
|---|---|---|---|
| 10 | 0.94 | 0.95 | 0.95 ± 0.01 |
| 20 | 0.89 | 0.91 | 0.90 ± 0.01 |
| 30 | 1.07 | 1.23 | 1.15 ± 0.08 |
| 40 | 1.07 | 1.09 | 1.08 ± 0.01 |
| 50 | 1.19 | 1.23 | 1.21 ± 0.02 |
| 60 | 1.19 | 1.25 | 1.22 ± 0.03 |
| 70 | 1.21 | 1.27 | 1.24 ± 0.03 |
| 80 | 1.11 | 1.24 | 1.18 ± 0.06 |
| 90 | 1.28 | 1.26 | 1.27 ± 0.01 |
| 100 | 1.23 | 1.25 | 1.24 ± 0.01 |
| 110 | 1.42 | 1.24 | 1.33 ± 0.09 |

TABLE 4-continued

Mean Drug Content Uniformity
Mean Drug Content Uniformity (mg/spray)

| Number of Sprays | Vial 1 | Vial 2 | Mean ± SEM |
|---|---|---|---|
| 120 | 1.48 | 1.21 | 1.34 ± 0.14 |
| 130 | 0.92 | 1.12 | 1.02 ± 0.10 |

EXAMPLE 5

Biodistribution of Compositions Containing R(+)-N-[3-[5-(4-fluorophenoxy)-2-furanyl]-1-methyl-2-propynyl]-N-hydroxyurea A SLS (sodium lauryl sulfate) MDI formulation was tested in the following biodistribution study. One group of 13 male Sprague-Dawley rats, weighing 400 to 500 grams was used. This group of animals was dosed with a sodium lauryl sulfate-based R(+)-N-[3-[5-(4-fluorophenoxy)-2-furanyl]-1-methyl-2-propynyl]-N-hydroxyurea MDI formulation. Blood samples were collected at 0.083, 0.25, 0.5, 1, 2, 4 and 6 hours after dosing. One animal in each group was sacrificed at 0.25, 0.5, 1, 2, 4 and 6 hours after dosing for the determination of drug concentrations in the lung. The SLS-based inhalation formulation was found to deliver about 26% of the nominal dose to the lungs. Following the delivery of the SLS-based formula, high drag concentrations of about 67 μg/g were recovered from the lung. Data collected at subsequent time points indicated sustained drug concentrations of 10 to 14 μg/g in the lung and about 0.2 mg/mL drug levels in the blood over 6 hours after dosing. The results are shown in Table 5. The data show that MDI formulations of R(+)-N-[3-[5-(4-fluorophenoxy)-2-furanyl]-1-methyl-2-propynyl]-N-hydroxyurea in HFA-134a can be reproducibly delivered.

TABLE 5

Drug Concentrations in Lung and Blood of R(+)-N-[3-[5-(4-fluorophenoxy)-2-furanyl]-1-methyl-2-propynyl]-N-hydroxyurea Using an SLS MD[(a)] in Rats

| | Concentrations of Drug | |
|---|---|---|
| Time (hr) | Lung (μg/g) | Blood (μg/mL) |
| 0 | 66.74[(b,c)] | —[(d)] |
| 0.083 | —[(d)] | 0.11 ± 0.08 (n = 12) |
| 0.25 | 14.46 ± 6.33 | 0.14 ± 0.07 (n = 12) |
| 0.5 | 12.12 ± 4.72 | 0.18 ± 0.08 (n = 9) |
| 1.0 | 13.08 ± 15.7 | 0.18 ± 0.06 (n = 8) |
| 2.0 | 16.64 ± 13.0 | 0.15 ± 0.06 (n = 6) |
| 4.0 | 8.54 ± 3.10 | 0.20 ± 0.04 (n = 4) |
| 6.0 | 9.85 ± 2.91 | 0.28 ± 0.27 (n = 2) |

[(a)]Composition: 10 mg/mL drug and 0.3% SLS (sodium lauryl sulfate) in HFA-134a.
[(b)]Only one animal per time-point.
[(c)]26.7% of theoretically delivered drug.
[(d)]Not determined.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the substituents, means of preparation and/or methods of use of the invention, may be made without departing from the spirit and scope thereof.

What is claimed is:

1. A pharmaceutical composition for aerosol delivery consisting essentially of a medicament, a non-chlorofluorocarbon propellant as the sole propellant, and a detergent, wherein the medicament is present as a solid dispersion in a concentration of between about 0.001 mg/ml and about 100 mg/ml, the detergent is present in a concentration of between about 0.00001% and about 10% by weight, and the non-chlorofluorocarbon propellant is selected from the group consisting of HCFC 123, HCFC 124, HCFC 141b, HCFC 225, HCFC 125, perfluorodimethylcyclobutane, DYMEL A, DYMEL 152a, HFC 134a and HFC 227ea, with the proviso that the pharmaceutical composition does not contain additional alcohol, a surfactant or a cosolvent.

2. A pharmaceutical composition according to claim 1 wherein the detergent is selected from the group consisting of substituted, mixed, and esterified organic alcohols; substituted and mixed organic acids; substituted alkylsulfates; substituted alkylsulfonates; alkylsulfosuccinates; cholic acid derivatives; glyceride esters of fatty acids; glyceride esters of polyethylene glycol acids; polyoxyethylene ethers, alcohols and esters; alkyl-substituted sorbitol esters and ethers with organic acids; stearates; and substituted organic stearates.

3. A pharmaceutical composition according to claim 2 wherein the propellant is selected from the group consisting of HFC-134a and HFC-227ea.

4. A pharmaceutical composition according to claim 1 wherein the detergent is selected from the group consisting of hydroxyzed poly(vinyl alcohol)s, phosphatidic acid, cholesterol, tripalmitin (glyceryl tripalmitate), and biological detergents.

5. A pharmaceutical composition according to claim 4 wherein the detergent is a biological detergent selected from the group consisting of anionic detergents, zwitterionic detergents and polyoxyethylene ether nonionic detergents.

6. A pharmaceutical composition according to claim 1 wherein the biological detergent is an anionic detergent selected from the group consisting of aerosol 22, alkylsulfonic acids, hydrolyzed poly(vinyl alcohol), sodium lauryl sulfate, phosphatidic acid, cholesterol, tripalmitin and decanesulfonic acidhydrolyzed poly(vinyl alcohol), cholesterol, sodium lauryl sulfate, stearic acid, caprylic acid, cholic acid, glycocholic acid, taurocholic acid, deoxycholic acid, glycodeoxycholic acid, taurodeoxycholic acid, polidocanol, polyoxyethylene 4-lauryl ether, polyoxyethylene 10-lauryl ether, 1-pentanesulfonic acid, 1-octanesulfonic acid, 1-nonanesulfonic acid, 1-decanesulfonic acid, N-decyl-N,N-dimethyl-3-ammonio-1-propanesulfonic acid, (3-[(3-cholamidopropyl)-dimethylammonio]-1-propanesulfonic acid, (3-[(3-cholamidopropyl)-dimethylammonio]-2-hydroxy-1-propanesulfonic acid, and N-hexadecyl-N,N-dimethyl-3-ammonio-1-propanesulfonic acid.

7. A pharmaceutical composition according to claim 4 wherein the propellant is selected from the group consisting of HFC-134a and HFC-227ea.

8. A pharmaceutical composition according to claim 1 wherein the detergent is present in a concentration of between 0.001% and 5% by weight.

9. A pharmaceutical composition according to claim 8 wherein the medicament is selected from the group consisting of LHRH analogs and 5-lipoxygenase inhibitors.

10. A pharmaceutical composition according to claim 1 wherein the medicament is an LHRH analog.

11. A pharmaceutical composition according to claim 1 wherein the medicament is leuprolide acetate.

12. A pharmaceutical composition according to claim 11 wherein the propellant is HFC-134a.

13. A pharmaceutical composition according to claim 11 wherein the detergent is selected from the group consisting of hydrolyzed poly(vinyl alcohol), sodium lauryl sulfate, phosphatidic acid, cholesterol, tripalmitin and decanesulfonic acid.

14. A pharmaceutical composition according to claim 13 wherein the detergent is selected from the group consisting of sodium lauryl sulfate, cholesterol, tripalmitin and decanesulfonic acid.

15. A pharmaceutical composition according to claim 13 wherein the detergent is present in a concentration of between 0.001% and 5% by weight.

16. A pharmaceutical composition according to claim 1 wherein the medicament is a 5-lipoxygenase inhibitor.

17. A pharmaceutical composition according to claim 1 wherein the medicament is selected from the group consisting of R(+)-N-[3-[5-(4-fluorophenoxy)-2-furanyl]-1-methyl-2-propynyl]-N-hydroxyurea and R(+)-N-[3-[5-(4-fluorophenoxy)-thiophen-2-yl]-1-methyl-2-propynyl]-N-hydroxyurea.

18. A pharmaceutical composition according to claim 17 wherein the propellant is HFC-134a.

19. A pharmaceutical composition according to claim 17 wherein the detergent is selected from the group consisting of aerosol 22, hydrolyzed poly(vinyl alcohol), cholesterol, sodium lauryl sulfate, stearic acid, caprylic acid, cholic acid, glycocholic acid, taurocholic acid, deoxycholic acid, glycodeoxycholic acid, taurodeoxycholic acid, polidocanol, polyoxyethylene 4-lauryl ether, polyoxyethylene 10-lauryl ether, 1-pentanesulfonic acid, 1-octanesulfonic acid, 1-nonanesulfonic acid, 1-decanesulfonic acid, N-decyl-N,N-dimethyl-3-ammonio-1-propanesulfonic acid, (3-[(3-cholamidopropyl)-dimethylammonio]-1-propanesulfonic acid, (3-[(3-cholamidopropyl)-dimethylammonio]-2-hydroxy-1-propanesulfonic acid, and N-hexadecyl-N,N-dimethyl-3-ammonio-1-propanesulfonic acid.

20. A pharmaceutical composition according to claim 19 wherein the detergent is selected from the group consisting of cholesterol, sodium lauryl sulfate, stearic acid, caprylic acid, taurocholic acid, taurodeoxycholic acid, 1-octanesulfonic acid, 1-nonanesulfonic acid, N-decyl-N,N-dimethyl-3-ammonio-1-propanesulfonic acid, (3-[(3-cholamidopropyl)-dimethylammonio]-1-propanesulfonic acid and (3-[(3-cholamidopropyl)-dimethylammonio]-2-hydroxy-1-propanesulfonic acid.

21. A pharmaceutical composition according to claim 20 wherein the detergent is selected from the group consisting of cholesterol, sodium lauryl sulphate, stearic acid, caprylic acid and taurocholic acid.

22. A pharmaceutical composition according to claim 19 wherein the detergent is present in a concentration of between 0.001% and 5% by weight.

* * * * *

UNITED STATES PATENT AND TRADEMARK OFFICE
CERTIFICATE OF CORRECTION

PATENT NO.    : 5,676,931
DATED         : October 14, 1997
INVENTOR(S)   : Adjei et al.

It is certified that error appears in the above-identified patent and that said Letters Patent is hereby corrected as shown below:

In the title, line [54], change "NON CFC" to --NON-CFC--.

Column 10, line 17, change "A." to --A,--.

Signed and Sealed this

Twenty-first Day of April, 1998

Attest:

BRUCE LEHMAN

Attesting Officer        Commissioner of Patents and Trademarks